| United States Patent [19] | [11] | 4,328,352 |
|---|---|---|
| Oppolzer | [45] | May 4, 1982 |

[54] PROCESS FOR MAKING NORPATCHOULENOL AND NOVEL INTERMEDIATES USEFUL THEREIN

[75] Inventor: Wolfgang Oppolzer, Vandoeuvres, Switzerland

[73] Assignee: Givaudan Corporation, Clifton, N.J.

[21] Appl. No.: 189,254

[22] Filed: Sep. 22, 1980

Related U.S. Application Data

[62] Division of Ser. No. 64,445, Aug. 6, 1979, Pat. No. 4,277,631.

[30] Foreign Application Priority Data

Aug. 10, 1978 [CH] Switzerland ............... 8520/78

[51] Int. Cl.³ .............................................. C07F 7/18
[52] U.S. Cl. .................................................. 556/436
[58] Field of Search ......................................... 556/436

[56] References Cited

U.S. PATENT DOCUMENTS 4,077,996  3/1978  Sauer et al. .................... 556/436 X

*Primary Examiner*—Paul F. Shaver
*Attorney, Agent, or Firm*—Robert F. Tavares

[57] ABSTRACT

A novel norpatchoulenol synthesis is disclosed. The key step in the synthesis is an intramolecular Diels-Alder condensation of a trisubstituted silyloxy derivative of cyclohexadienone. Novel intermediates, namely trisubstituted silyloxy methanonaphthalenes (Formula V, infra) and trisubstituted silyloxy cyclohexadienes (Formula IV, infra) are prepared.

4 Claims, No Drawings

PROCESS FOR MAKING NORPATCHOULENOL AND NOVEL INTERMEDIATES USEFUL THEREIN

This is a division of application Ser. No. 64,445 filed Aug. 6, 1979, now U.S. Pat. No. 4,277,631.

FIELD OF THE INVENTION

The invention relates to the fields of perfumery and organic chemical synthesis.

BACKGROUND OF THE INVENTION

Norpatchoulenol, having the formula

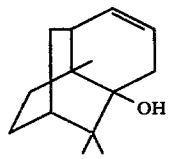

VIII is a component of patchouli oil. It is present therein only in very small amounts, but is nevertheless the main olfactory vector of patchouli oil. Norpatchoulenol can be used for the preparation of perfumes and odoriferous compositions, whereby in many cases norpatchoulenol is better suited for this purpose than patchouli oil itself. It is therefore desirable to be able to obtain norpatchoulenol in a pure state, free from other ingredients, some of which are obnoxious, which occur in patchouli oil. The first synthesis of norpatchoulenol was described in "Recherches", (Roure Bertrand Dupont) 19 (1974) 69. This synthesis is, however, a relatively complicated one involving many steps. A further route to norpatchoulenol starts from patchouli alcohol which is contained in patchouli oil in much larger amounts (about 40%). Patchouli alcohol can be converted into norpatchoulenol by microbiological hydroxylation (DOS 2 739 449) followed by oxidative decarboxylation (DOS 2 529 603). This synthesis is, however, dependent, just the same as before, on patchouli oil produced from nature.

PRESENT INVENTION

The present invention is concerned with a process for the production of substituted 5,5,8a-trimethyl-1,6methanonaphthalenes, which comprises intramolecularly cyclising a compound of the formula

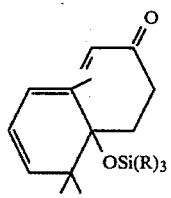

IV wherein R signifies a lower alkyl, phenyl, lower, alkylphenyl or phenyllower alkyl group, wherein the lower alkyl groups contain from 1 to 4 carbon atoms, to give a compound of the formula

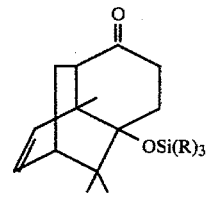

V and subsequently if desired, in any order, splitting off the trisubstituted silyl group, hydrogenating the 7,8-double bond to a single bond and forming a hydrazone derivative of the thus-formed 4-keto compound followed by decomposition of the hydrazone to form a 3,4-double bond, to yield norpatchoulenol.

DESCRIPTION OF THE PREFERRED EMBODIMENTS

The various steps whereby the compounds of the formula V can be converted into norpatchoulenol can conveniently be carried out in the following sequence: (a) removal of the trisubstituted silyl group, (b) hydrogenation of the 7,8-double bond and (c) removal of the 4-keto function with introduction of the 3,4-double bond. These steps can, however, also be carried out in any other desired order.

The substituents R may be the same or different from one another and represent, for example, methyl, ethyl, propyl, butyl, phenyl, benzyl or tolyl. Preferably, the substituents R are in each case the same and represent methyl or ethyl.

The intramolecular cyclisation can be carried out in the gas phase or in the liquid phase. When carrying out the cyclisation in the liquid phase, it is conveniently effected in solution in an organic solvent. The solvent may be an aromatic of aliphatic hydrocarbon or a chlorinated hydrocarbon, e.g. benzene, toluene, heptane, decane or chlorobenzene.

In the liquid phase the intramolecular cyclisation is conveniently carried out at temperature between about 200° and about 300° C., whereby the preferred temperature range lies between 220° and 250° C. At higher temperatures the yields are generally lower. At a temperature of about 230° C. the reaction takes about 12 hours.

The intramolecular cyclisation in the gas phase can be carried out at temperatures in the range between about 500° and about 800° C. In this case the reaction time generally amounts to less than 2 seconds, preferably about 0.5 seconds. The reaction in the gas phase is conveniently carried out in a quartz tube.

The cleavage-off of the trisubstituted silyl group is conveniently carried out using mild acid hydrolysis, for example, by means of a weak organic acid, such as dilute acetic acid. This reaction is conveniently effected in solution in an organic solvent.

The 7,8-double bond is conveniently hydrolysed with the use of a noble metal catalyst. As such a catalyst there can be used, for example, a platinum catalyst or a palladium catalyst, e.g. platinum oxide.

The removal of the 4-keto group and the introduction of the 3,4-double bond can conveniently be carried out in a manner known per se with the use of the Bamford-Stevens reaction, i.e. by first forming a hydrazone derivative, for example a p-toluenesulphonylhydrazone derivative, which is then cleaved off [Org. Reactions 23 (1976) 405].

The starting material of the formula IV can be manufactured in a manner known per se, for example by treatment of a 2,2,6-trimethylcyclohexa-2,4-dienone with a 3-trisubstituted silyloxydienyl-lithium of the formula

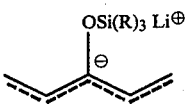
II wherein R has the above significance, and the dotted lines indicated the presence of two conjugated double bonds, and subsequent treatment of the resulting product with a trisubstituted silyl halide, preferably a tri(lower alkyl)-silyl halide, for example trimethylsilyl chloride, to give the tetraene of formula

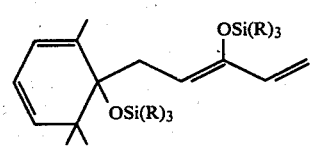
III

The selective desilylation of this tetraene with potassium fluoride in methanol at a temperature between about 0° and 5° C. gives, after chromatography, the desired starting material of formula

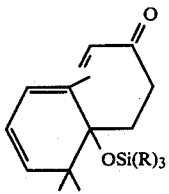
IV

The methanonaphthalenes of formula

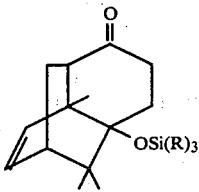
V and also the substituted cyclohexadienes of the formula

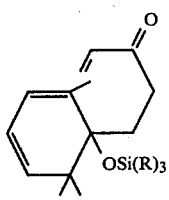
IV are novel compounds and as such are likewise an object of the present invention.

The complete path of the synthesis of norpatchoulenol starting from 2,2,6-trimethylcyclohexa-2,4-dienone may be represented schematically as follows:

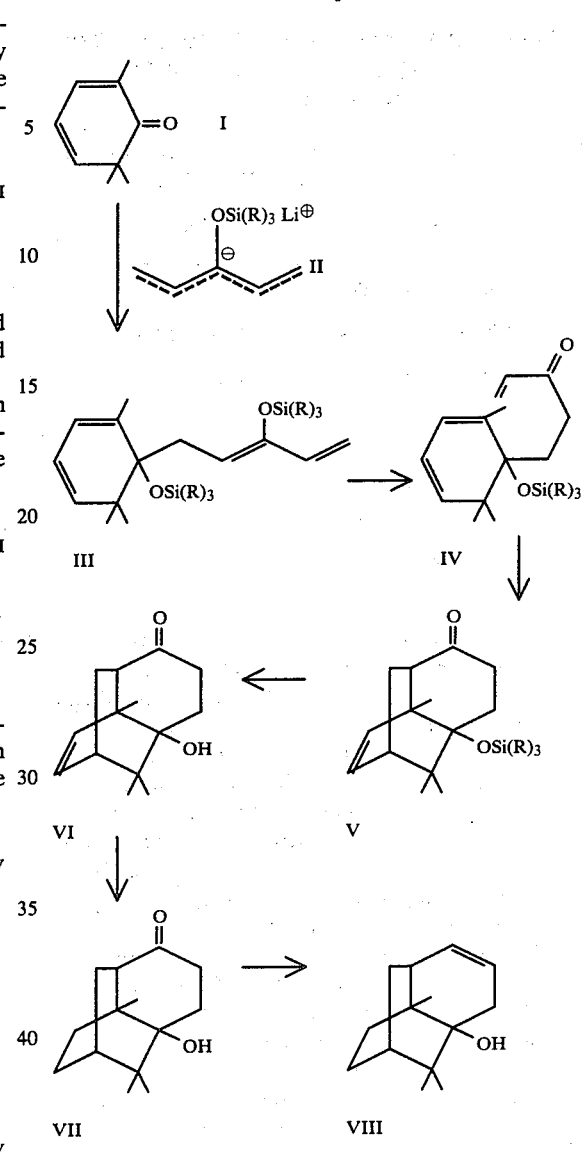

The process in accordance with the invention makes it possible to manufacture not only (±), but also (+), as well as (−)-norpatchoulenol depending on the configuration of the starting material of the formula IV used. With the use of an optically active starting material there is accordingly obtained an optically active end product. For the manufacture of the (+)-norpatchoulenol, as it is present in natural patchouli oil, there is to be used a trisubstituted silyl compound of the formula IV which is present in the S-configuration.

EXAMPLE 1

A solution of 20 mg of 1-[3-oxo-pent-4-en-1-yl]-1-trimethylsilyloxy-2,2,6-trimethylcyclohexa-2,4-diene in 6.6 ml of absolute benzene was sealed in a silylated (i.e. treated with bissilylacetamide) Pyrex ampoule, heated at 230° C. for 12 hours and subsequently filtered over silica gel (with $CH_2Cl_2$). The evaporated eluate gave 15.2 g of 1,2,3,4,4a,5,6,8a-octahydro-2-oxo-4a-trimethylsilyloxy-5,5,8a-trimethyl-1,6-methanonaphthalene (76% yield, m.p. 73°–76° C.).

The starting material can be manufactured by one of the two following methods (a) A solution of 2 mmol of freshly prepared 3-triethylsilyloxypentadienyl-lithium in 4 ml of tetrahydrofuran was added dropwise at −78° C. to a stirred solution of 272 mg of 2,2,6-trimethylcyclohexa-2,4-dienone in 2 ml of tetrahydrofuran. The reaction mixture was stirred at −78° C. for 5 minutes, then treated with 1 ml of hexamethylphosphoric acid triamide, subsequently treated with 0.4 ml of trimethylsilyl chloride (0.4 ml), stirred at −78° C. for a further hour and finally poured into saturated aqueous NH$_4$Cl solution. Extraction with pentane and evaporation of the dried extract gave a colourless oil which was dissolved in 30 ml of methanol. 400 mg of potassium fluoride were added portionwise at 0° C. under argon and while stirring. The mixture was stirred at 0° to 5° C. for 1 hour, subsequently poured into saturated aqueous NH$_4$Cl solution and extracted with ether. Chromatography of the evaporated extract (kieselgel, 15 g/-CH$_2$Cl$_2$) gave 276 mg of 1-[3-oxo-pent-4-en-1-yl]-1-trimethylsilyloxy-2,2,6-trimethylcyclohexa-2,4-diene (47% yield), colourless oil, IR(CCl$_4$): 1710, 1693, 1625, 1258, 1130, 905 cm$^1$).

(b) To a solution of 400 mg 3-trimethylsilyloxy-1,4-pentadiene in 3 ml of tetrahydrofuran at −78° under argon was added a solution of 2.3 ml of sec-butyllithium in cyclohexane and the solution stirred for 15 minutes. Then, a solution of 275 mg. of 2,6,6-trimethylcyclohexa-2,4-dienone in 1 ml of tetrahydrofuran was added. After 5 minutes, 332 mg of trimethylsilyl chloride in 2 ml of hexamethylphosphoric acid triamide was added and the mixture left for 1 hour at −78°. After working up as in Example 1(a) the crude product mixture was diluted with 20 ml of methanol cooled to 0° and 224 mg of potassium fluoride were added. After 1 hour at 0°–5°, the mixture was poured into saturated aqueous NH$_4$Cl solution and extracted with ether. Chromatography (SiO$_2$, toluene) of the evaporated extract gave 329 mg of 1-[3-oxo-pent-4-en-1-yl]-1-trimethylsilyloxy-2,6,6-trimethylcyclohexa-2,4-diene (56% yield) characteristics as above.

EXAMPLE 2

A solution of 21 mg of 1,2,3,4,4a,5,6,8a-octahydro-2oxo-4a-trimethylsilyloxy-5,5,8a-trimethyl-1,6-methanonaphthalene in 4 ml of acetic acid/tetrahydrofuran/water (3:1:1) was stirred under argon at 25° C. over 10 hours, then poured into saturated aqueous NaHCO$_3$ solution and extracted with CH$_2$Cl$_2$. After chromatography (SiO$_2$, ethyl acetate/CH$_2$Cl$_2$) and sublimation, there were obtained 15 mg of 1,2,3,4,4a,5,6,8a-octahydro-2-oxo-4a-hydroxy-5,5,8a-trimethyl-1,6-methanonaphthalene (m.p. 112°–115° C., 95% yield).

EXAMPLE 3

22 mg of 1,2,3,4,4a,5,6,8a-octahydro-2-oxo-4a-hydroxy-5,5,8a-trimethyl-1,6-methanonaphthalene in 4 ml of ethanol is stirred in the presence of 6 mg of PtO$_2$ for 12 hours under a H$_2$ atmosphere (1 atm, 25° C.). The reaction mixture, filtered through Celite and evaporated, gave, after chromatography and sublimation, 20.5 mg of 1,2,3,4,4a,5,6,7,8,8a-decahydro-2-oxo-4a-hydroxy-5,5,8a-trimethyl-1,6-methanonaphthalene (m.p. 120°–123° C., 92% yield).

EXAMPLE 4

9.3 mg of N-toluenesulphonylhydrazide was added to a solution of 11.1 mg of 1,2,3,4,4a,5,6,7,8,8a-decahydro-2-oxo-4a-hydroxy-5,5,8a-trimethyl-1,6-methanonaphthalene in hot acetic acid. The mixture was refluxed for 10 minutes, subsequently poured into saturated aqueous NaHCO$_3$ solution, extracted with CH$_2$Cl$_2$ and evaporated. The solution of the residue in 4 ml of ether was treated slowly at 25° C. with a 1-N solution of methyllithium in ether (0.225 ml), then stirred at 25° C. under argon, then poured into water and extracted with CH$_2$Cl$_2$. Chromatography (SiO$_2$/CH$_2$Cl$_2$) and sublimation at 100°–120° C. gave (+)-norpatchoulenol (m.p. 135°–141° C., 6.8 mg, 68% yield).

I claim:

1. Methanonaphthalenes of the formula

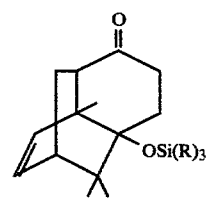

V wherein R represents a lower alkyl, phenyl, lower alkylphenyl or phenyllower alkyl group, wherein the lower alkyl groups contain from 1 to 4 carbon atoms.

2. Methanonaphthalenes according to claim 1, wherein R represent methyl or ethyl.

3. Substituted cyclohexadienes of the formula

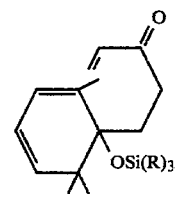

IV wherein R represents a lower alkyl, phenyl, lower alkylphenyl or phenyllower alkyl group, wherein the lower alkyl groups contain from 1 to 4 carbon atoms.

4. Substituted cyclohexadienes according to claim 3, wherein R represents methyl or ethyl.

* * * * *